United States Patent [19]
Gonçalves

[11] Patent Number: 5,901,707
[45] Date of Patent: *May 11, 1999

[54] SILICONE MASK FOR CRYOSURGERY AND METHOD

[75] Inventor: J.C. d'Almeida Gonçalves, Santerem, Portugal

[73] Assignee: HPL Biomedical, Inc., Las Vegas, Nev.

[ * ] Notice: This patent issued on a continued prosecution application filed under 37 CFR 1.53(d), and is subject to the twenty year patent term provisions of 35 U.S.C. 154(a)(2).

[21] Appl. No.: 08/445,089

[22] Filed: May 19, 1995

[51] Int. Cl.$^6$ .............................. A61B 19/08; A61B 17/36
[52] U.S. Cl. .............................. 128/853; 128/849; 606/22
[58] Field of Search .................................. 606/22, 23, 1, 606/20; 128/849, 853; 602/41–59

[56] References Cited

U.S. PATENT DOCUMENTS

| | | | |
|---|---|---|---|
| 3,658,066 | 4/1972 | Saidi et al. | 606/23 |
| 4,601,286 | 7/1986 | Kaufman | 128/849 |

FOREIGN PATENT DOCUMENTS

| | | | |
|---|---|---|---|
| 546373 | 9/1957 | Canada | 128/853 |

*Primary Examiner*—Glenn K. Dawson
*Attorney, Agent, or Firm*—Michael G. Petit

[57] ABSTRACT

A cryosurgery mask permits the continuous application of coolant during cryosurgery. Cryosurgery employs the application of a coolant, such as liquid nitrogen (LN), to a target tissue to effect the removal thereof. The target tissue normally includes diseased tissue, along with a safety margin of adjacent tissue. The cryosurgery mask includes a flexible sheet having a non-adhesive upper surface and a lower skin-facing surface of a silicone gel composition which remains adherent to skin at cryosurgery temperature. A release film is releasably affixed to the skin-facing surface to protect against contamination. In operation, a hole, dimensioned to encircle both the diseased tissue and a safety margin of adjacent normal tissue, is removed from the sheet. The release film is removed and the hole is positioned over the target tissue. The gel layer adjacent to and surrounding the hole is pressed against the skin. A constant spray of LN may then be applied to the target tissue to effect freezing. The gel surface adheres to the skin forming a barrier and preventing LN from freezing non-target tissue. The mask permits the rapid cooling of diseased tissue to a desired depth, while minimizing damage to non-target tissue.

5 Claims, 1 Drawing Sheet

SILICONE MASK FOR CRYOSURGERY AND METHOD

BACKGROUND OF THE INVENTION

1. Field of the Invention

This invention relates to an improved method for performing cryosurgery and, more particularly, to a mask or drape having a silicone gel surface which adheres to the skin at low temperatures.

2. Prior Art

Cryotherapy is a well established procedure for removing unwanted tissue (target tissue) from the skin. The advantages of treating target tissue such as a tumor with cryosurgery include a higher cure rate and reduced cost per procedure. Small tumors take less than 20 minutes to freeze while larger cancers (i.e. breast and vulva) can take up to 3 hours. In addition, healthy skin can tolerate temperatures down to −12° centigrade. Problems occur when the temperature gets below −20° C. In cryosurgery, an area of the skin incorporating the unwanted or diseased tissue is frozen to reduce the temperature of the tissue to a lethal temperature causing cell death in the diseased tissue which is subsequently rejected by the body. A safety margin consisting of normal tissue adjacent to and surrounding the diseased tissue is also frozen to prevent any diseased tissue cells from remaining behind.

When performing cryosurgery it is desirable to "freeze quickly and thaw slowly." In accordance with this dictum, liquid nitrogen is a preferred coolant and is widely employed for freezing unwanted target tissue. Liquid nitrogen (LN) is relatively inexpensive and easy to handle. The disadvantage of using liquid nitrogen is that when LN is applied to the surface of the skin it freezes the outermost layer before cooling the target tissue to a depth sufficient to kill all diseased cells. The frozen layer of skin forms a barrier to heat conduction causing additional LN applied to the target tissue to run off the frozen surface surrounding nontarget tissue before it can evaporate. To prevent such damage to nontarget tissue, practitioners use intermittent spraying of coolant onto the target tissue. This enables the heat to be conducted from the deeper tissue to the outer layer where the caloric content is expended vaporizing the liquid nitrogen and equilibrating the tissue temperature to a desired depth. Thus, in order to prevent inadvertent burning of nontarget tissue, an intermittent spray is employed.

Silicone sheeting has been used for many years as a wound dressing. There are other medical conditions, such as burns, which benefit by the application of silicone sheeting thereto. In some instances, the silicone sheeting is permeable to liquids so that a suppurating wound may remain dry. In other instances, the sheeting is permeable to gases. Unfortunately, the currently available sheeting used for wound dressing is inoperable as a mask for cryosurgery because either the sheeting is permeable to gas and/or liquids or the surface of the sheeting (which contacts the skin) comprises a gel which loses its ability to adhere to the skin at temperatures below −20° C. As a consequence, the material used in commercially available silicone gel type wound dressings, such as "Epi-Derm®", does not provide a suitable masking material for enabling the practitioner to use a constant stream of liquid nitrogen to freeze unwanted tissue without injury to non-target tissue.

SUMMARY OF THE INVENTION

It is an object of this invention to provide a silicone sheeting suitable for the protective masking of normal tissue adjacent to target diseased tissue against thermal damage during cryosurgery of the diseased target tissue.

It is another object of this invention to provide a method for performing cryosurgery wherein the diseased target tissue may be frozen quickly.

It is still another object of this invention to provide a masking material suitable for protecting normal tissue while performing cryosurgery in which the upper non-skincontacting surface of the masking material does not adhere to surgical gloves.

The features of the invention believed to be novel are set forth with particularity in the appended claims. However, the invention itself both as to organization and method of operation together with further objects and advantages thereof, will best be understood with reference to the following description taken in conjunction with the accompanying drawings in which:

DETAILED DESCRIPTION OF THE PREFERRED EMBODIMENTS

Figure 1:
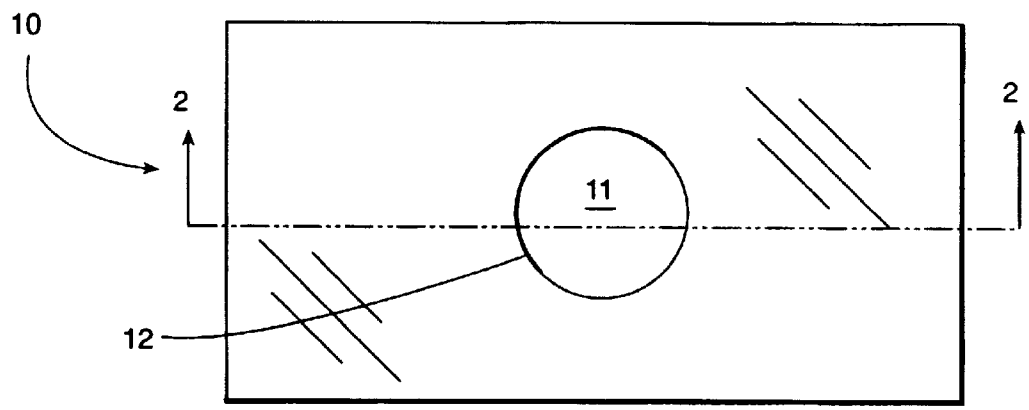
FIG. 1 is a top plan view of a cryosurgery mask in accordance with the present invention.

A sheet of gel containing masking material, in accordance with the present invention, is shown at 10 in FIG. 1. The sheet 10 has an aperture 11 cut therein, which aperture is dimensioned to encircle a target tissue to be removed by cryosurgery. The outer margin 12 of the aperture 11 includes a safety zone around the target tissue to ensure complete removal of target tissue. For the purpose of further exposition of the invention, the mask 10 will be said to have an upper surface which, in operation, faces away from the patient's skin; the opposing surface being the lower surface which faces the skin. All the individual films or layers comprising the mask will also have upper and lower surfaces which face in the same direction as the corresponding surfaces on the mask 10.

Figure 2:
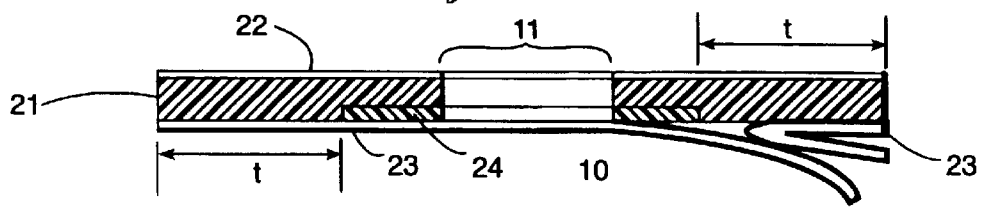
FIG. 2 is a cross-sectional view of the cryosurgery mask of FIG. 1 taken along section line 2—2.

The sheet 10 is seen in cross-section along section line 2—2 in FIG. 2. The sheet 10 comprises a film layer 21 which provides structural integrity and coherence to the mask 10. Although cured silicone sheeting is a preferred elastomer for the film 21, other polymer films, particularly fluoropolymer films which are not adherent to surgical gloves, may be employed. The film layer 21 of the sheet 10 has an upper surface 22. The upper surface 22 may simply be the upper surface of a non-adherent film material or it may be a non-sticky coating applied to a sticky film material. It is important that the upper surface 22 of the mask 10 be non-adherent to surgical rubber gloves in order to facilitate placement of the mask against the skin. The lower surface of the film layer 21 must be adherent to silicone gel. In the center of the sheeting 10, an aperture 11 is shown. The lower surface of the sheet 10 has a release film 23 affixed hereto. In operation, the release film 23 is peeled off of the skin-contacting portions 21 and 24 of the sheet 10 to expose the adhesive gel of the mask 10. The adhesive gel layer, indicated at 24 in FIG. 2, is the portion of the skin-contacting surface of the mask surrounding and adjacent to the aperture 11. The adhesive gel layer 24 has the property that the gel is adhesive to skin even when cooled to temperatures as low as −50° C. which are attained at the skin surface during cryosurgery.

Non-perforated silicone sheeting has been used to treat keloids—(Epi-Derm® available from Biodermis Corporation, Las Vegas, Nev.). The sheeting has a lower surface consisting of a silicone gel which adheres to the skin. This sheeting appeared to be a useful thermal masking material for cryosurgery, where the ice front could be restricted to only target tissue.

To test this silicone gel sheeting's utility as a mask in cryosurgery, a hole was punched in the center of a Epi-Derm® silicone sheet (SS) and two thermocouples placed 3 mm and 5 mm from the hole. LN spray was applied to the mask adjacent to the hole and sub-freezing temperatures were not observed on either thermocouple. Next, a patient's skin was cleaned with ether around a basal-cell carcinoma. An aperture dimensioned to accommodate the tumor therewithin (plus a safety margin) was cut through the SS to create a thermal mask. The mask was then applied to the patent's skin along with two thermocouples; one thermocouple positioned directly under the tumor and the other thermocouple positioned under its margin. Continuous LN spray from a Frigitronics apparatus CD 4G was applied to the tumor underlying the aperture. As the target tissue was cooled, the SS gel layer lost its ability to adhere to the skin and the pressure from the LN spray caused the gel surface of the mask to detach from the skin for nearly 10 mm around the aperture. The procedure was discontinued.

The manufacturer was contacted and was asked to prepare similar silicone sheets with enhanced adherence at low temperature. Three samples with code names were provided by the manufacturer excluding any information about the composition and adherence of the gel layer. Blind trials were conducted. One gel was found to adhere to the skin during cooling even when subjected to the pressure of the spray.

The prepared gel was identified by the manufacturer as a high strength silicone gel consisting of a two-part system of pure silicone polymers which, when mixed and cured, provide a gel having the requisite cohesiveness, transparency, strength and adherence at cryosurgery temperatures. Such a composition is commercially available from Applied Silicone Technology, Ventura, Calif., as part number 40022 and 40077. As stated above, this product is supplied in two parts: a base and a crosslinker. When mixed in the ratio of ten parts by weight of base to one part by weight of crosslinker and cured either at room temperature for 24 hours, or accelerated by elevated temperatures, a firm, and cohesive gel results. The cured gel is clear, colorless, and odorless, and can be formed into virtually any size and shape. The firmness of the gel can be controlled within a limited range by varying the crosslinker/base ratio. Heat cure cycles can be varied to suit the user's requirements. The firmness of the cured gel may be increased, i.e., a lower penetration value achieved, by increasing the proportion of crosslinker in the mix. The firmness may be decreased, i.e., a higher penetration value, by decreasing the proportion of crosslinker in the mix. Preferably, the crosslinker portion be limited to the range of 0.8 to 1.2 parts to 10 parts of base.

The mixture can be cured at room temperature or by application of heat. Time and temperature requirements will be dependent on the particular mix and can be readily optimized empirically.

A full cure is achieved after about 24 hours at room temperature. Full cure can be achieved in only 5 minutes at 150° C. The cure temperature can be adjusted to suit particular applications. Lower cure temperature may require greater time to achieve full cure. The resulting gel is transparent and has a viscosity of about 10,000–15,000 centipose. The cryosurgery mask has a construction similar to the familiar "BAND-AID" adhesive strip type of wound dressing with the strips gauze pad corresponding to the gel layer 24 and the peel-off film covering the adhesive layer of the strip corresponding to release film 23. As with the "BAND-AID" type of wound dressing, the releasing film 23 is affixed to the lower surface of the cryosurgery mask to form a material barrier which protects it from contamination prior to use.

Figure 3:
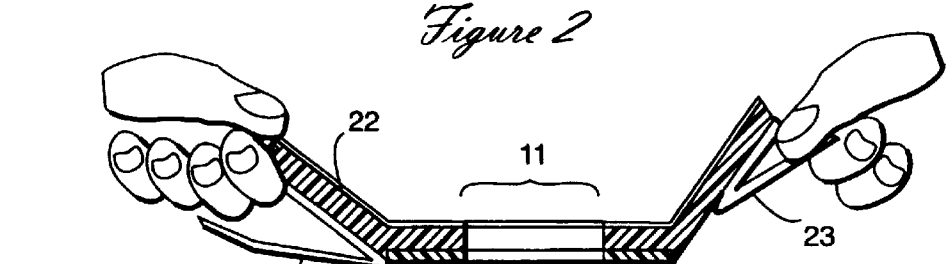
FIG. 3 is a side cross-sectional view of the cryosurgery mask in its preapplication position with the gel surface down and the protective release film in the process of removal.
Figure 4:
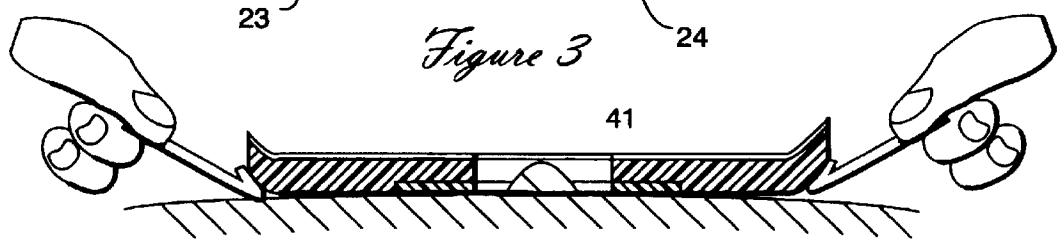
FIG. 4 is a side cross-sectional view, as in FIG. 3, showing the cryosurgery mask with the aperture positioned over the target tissue, prior to the application of coolant to the target tissue.
Figure 5:
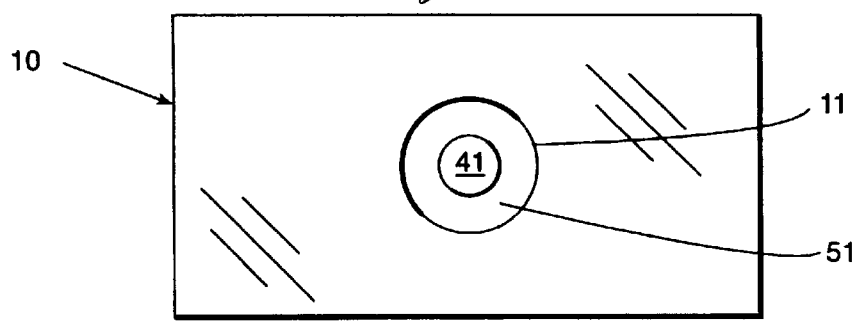
FIG. 5 is a top plan view of the mask in position with the protective release film on the skin facing (gel) surface removed, showing the aperture surrounding the unwanted target tissue.

As stated above, prior to applying the mask to the skin, the mask 10 is perforated to form the aperture 11 of the correct size to expose the diseased target tissue (plus a safety margin), then positioned over the patient's skin so that the aperture overlies the lesion to be removed (target tissue). The release film 23 is then removed from the lower skin contacting surface of the mask as shown in FIG. 3. The mask 10 is then lowered over the target tissue so that the target tissue lies completely within the aperture 11 as shown in FIG. 4. Once the mask is in position, as shown in FIG. 4, the mask is pressed firmly against the skin until the gel layer 24 adheres to the skin surrounding the target tissue 41. The top plan view of the mask, in position prior to cryosurgery, is shown in FIG. 5 wherein the target tissue 41 is centered within the aperture 11 with a safety zone 52 therearound.

Of 5 basal-cell carcinomas treated by cryosurgery employing the thermal mask described above, lethal temperatures of about −50° C. were quickly achieved by applying a continuous LN spray to the tumors. The peripheral spread of the ice front went beyond (undercut) the margin of the aperture by only 1 mm, and the gel layer of the mask remained adherent to the skin throughout the procedure. The rate of cooling of the target tissue is greatly enhanced by applying a continuous spray of coolant as compared with an intermittent open spray. After removal of the mask, the sharp limit of the resulting hypopigmentation can be prevented by "feathering" it, according to Zacarian. The foregoing method can be preceded by "debulking" the tumor with radio frequency to further shorten the operating time. The foregoing method for performing cryosurgery utilizing the cryosurgery mask has the further advantage in that the reduced intraoperative time compensates for the price of the mask as well as enabling compliance with a golden rule of cryosurgery: freeze quickly and thaw slowly.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What I claim is:

1. A cryosurgical mask for application to the skin of a patient wherein said skin includes a target tissue portion which is to be removed by cryosurgery, the mask being operable for protecting nontarget tissue adjacent to the target tissue from thermal damage resulting from cryosurgery on the target tissue portion, the mask comprising:

(a) a planar sheet of elastomeric material having an upper surface and a lower surface, said upper surface of said material being non-adherent to surgical gloves;

(b) a silicone gel layer covering at least a portion of said lower surface of said sheet and being adherent thereto, wherein said silicone gel layer is adherent to the skin at the temperature of −30° C. to −50° C.; and (c) a release film affixed to and covering at least a lower surface of the silicone gel layer, wherein the cryosurgical mask effectively protects tissue surrounding the target tissue portion from freezing, and thereby allows the target tissue portion to be continuously cooled.

2. The cryosurgical mask of claim 1, wherein the release film is releasably affixed to and covers the entire lower surface of the silicone gel layer and the lower surface of the planar sheet of elastomeric material.

3. The ciyosurgical mask of claim 1, wherein a user can form an aperture through portion of the silicone gel layer and the overlaying portions of the planar sheet of elastomeric material and release film; having a size and shape which is substantially identical to the size and shape olf said target tissue portion.

4. The cryosurgery mask of claim 1, wherein the planar sheet of elastomeric material comprises non-perforated silicone sheeting.

5. A method for performing cryosurgery to remove a target tissue from the surface of a patient's skin comprising the steps of:

(a) providing a generally planar surgical cryosurgery mask comprising a planar sheet of elastomer material havinig an upper surface being non-adherent to surgical gloves and a lower surface having a silicone gel layer which is adherent to the skin at a temperature of about −30° to −50° C. covering at least a portion of said lower surface, and a release film affixed to and covering a lower surface of said silicone gel layer;

(b) measuring said target tissue and cutting an aperture in said cryosurgical mask, said aperture being dimensioned to overlie said target tissue;

(c) removing said release film from said lower surface of said silicone gel layer;

(d) applying the cryosurgical mask to the patient's skin so that the target tissue is centered in the aperture; and (e) applying a freezing agent to the target tissue in a substantially continuous stream to affect lethal freezing of the target tissue.

* * * * *